United States Patent
Nieminen et al.

(10) Patent No.: US 11,215,457 B2
(45) Date of Patent: Jan. 4, 2022

(54) THEMATIC MAP BASED ROUTE OPTIMIZATION

(71) Applicant: Amer Sports Digital Services Oy, Vantaa (FI)

(72) Inventors: Heikki Nieminen, Vantaa (FI); Erik Lindman, Vantaa (FI); Tuomas Hapola, Vantaa (FI); Janne Kallio, Vantaa (FI)

(73) Assignee: Amer Sports Digital Services Oy, Vantaa (FI)

( * ) Notice: Subject to any disclaimer, the term of this patent is extended or adjusted under 35 U.S.C. 154(b) by 97 days.

(21) Appl. No.: 16/377,267

(22) Filed: Apr. 8, 2019

(65) Prior Publication Data

US 2019/0234741 A1    Aug. 1, 2019

Related U.S. Application Data

(63) Continuation-in-part of application No. 15/365,972, filed on Dec. 1, 2016, now Pat. No. 10,288,443.

(30) Foreign Application Priority Data

Dec. 1, 2015  (FI) ..................................... 20155906
Dec. 1, 2015  (GB) ..................................... 1521192

(51) Int. Cl.
  *G01C 21/20*  (2006.01)
  *G01C 21/36*  (2006.01)
  *G01C 21/34*  (2006.01)

(52) U.S. Cl.
  CPC .................................. *G01C 21/20* (2013.01)

(58) Field of Classification Search
  CPC ... G01C 21/20; G01C 21/3679; G01C 21/343
  (Continued)

(56) References Cited

U.S. PATENT DOCUMENTS 5,457,284 A    10/1995  Ferguson
5,503,145 A     4/1996  Clough
(Continued)

FOREIGN PATENT DOCUMENTS

AU    2007216704 A1    4/2008
CN       1877340 A1    12/2006
(Continued)

OTHER PUBLICATIONS

ARM big. LITTLE. Wikipedia, The free encyclopedia, Oct. 11, 2018, Retrieved on May 28, 2020 from: <https://en.wikipedia.org/w/index.php?title=ARM_bit.LITTLE&oldid=863559211> foreword on p. 1, section "Run-state migration" on pp. 1-2.
(Continued)

*Primary Examiner* — Yazan A Soofi
(74) *Attorney, Agent, or Firm* — Laine IP Oy

(57) ABSTRACT

According to an example aspect of the present invention, there is provided an apparatus comprising at least one processing core, at least one memory including computer program code, the at least one memory and the computer program code being configured to, with the at least one processing core, cause the apparatus at least to determine a route based at least partly on a thematic map database and a current location of the apparatus, present the determined route as a suggested route to a first user, and responsive to the first user approving the suggested route, initiate an activity session based on the suggested route.

17 Claims, 8 Drawing Sheets

(58) Field of Classification Search
USPC .......................................................... 701/426
See application file for complete search history.

(56) References Cited

U.S. PATENT DOCUMENTS

| | | | |
|---|---|---|---|
| 5,924,980 A | 7/1999 | Coetzee | |
| 6,882,955 B1 * | 4/2005 | Ohlenbusch | A43B 3/0005 702/160 |
| 7,627,423 B2 | 12/2009 | Brooks | |
| 7,706,973 B2 | 4/2010 | McBride et al. | |
| 7,721,118 B1 | 5/2010 | Tamasi et al. | |
| 7,917,198 B2 | 3/2011 | Ahola et al. | |
| 7,938,752 B1 | 5/2011 | Wang | |
| 8,052,580 B2 | 11/2011 | Saalasti et al. | |
| 8,323,188 B2 | 12/2012 | Tran | |
| 8,328,718 B2 | 12/2012 | Tran | |
| 8,538,693 B2 | 9/2013 | McBride et al. | |
| 8,612,142 B2 | 12/2013 | Zhang | |
| 8,655,591 B2 | 2/2014 | Van Hende | |
| 8,781,730 B2 | 7/2014 | Downey et al. | |
| 8,949,022 B1 | 2/2015 | Fahrner et al. | |
| 9,008,967 B2 | 4/2015 | McBride et al. | |
| 9,107,586 B2 | 8/2015 | Tran | |
| 9,222,787 B2 * | 12/2015 | Blumenberg | G01C 21/32 |
| 9,317,660 B2 | 4/2016 | Burich et al. | |
| 9,648,108 B2 | 5/2017 | Granqvist et al. | |
| 9,665,873 B2 | 5/2017 | Ackland et al. | |
| 9,829,331 B2 | 11/2017 | McBride et al. | |
| 9,830,516 B1 | 11/2017 | Biswas et al. | |
| 9,907,473 B2 | 3/2018 | Tran | |
| 9,923,973 B2 | 3/2018 | Granqvist et al. | |
| 10,234,290 B2 * | 3/2019 | Lush | G06F 3/0484 |
| 10,244,948 B2 * | 4/2019 | Pham | A61B 5/4866 |
| 10,327,673 B2 | 6/2019 | Eriksson et al. | |
| 10,415,990 B2 * | 9/2019 | Cho | G01C 21/3679 |
| 10,433,768 B2 | 10/2019 | Eriksson et al. | |
| 10,515,990 B2 | 12/2019 | Hung et al. | |
| 10,634,511 B2 | 4/2020 | McBride et al. | |
| 10,816,671 B2 | 10/2020 | Graham et al. | |
| 2003/0038831 A1 | 2/2003 | Engelfriet | |
| 2003/0109287 A1 | 6/2003 | Villaret | |
| 2005/0070809 A1 | 3/2005 | Acres | |
| 2005/0086405 A1 | 4/2005 | Kobayashi et al. | |
| 2006/0068812 A1 | 3/2006 | Carro et al. | |
| 2006/0136173 A1 | 6/2006 | Case et al. | |
| 2007/0156335 A1 | 7/2007 | McBride et al. | |
| 2007/0208544 A1 | 9/2007 | Kulach et al. | |
| 2007/0276200 A1 | 11/2007 | Ahola et al. | |
| 2008/0052493 A1 | 2/2008 | Chang | |
| 2008/0109158 A1 | 5/2008 | Huhtala et al. | |
| 2008/0136620 A1 | 6/2008 | Lee et al. | |
| 2008/0158117 A1 | 7/2008 | Wong et al. | |
| 2008/0214360 A1 | 9/2008 | Stirling et al. | |
| 2008/0294663 A1 | 11/2008 | Heinley et al. | |
| 2008/0318598 A1 * | 12/2008 | Fry | G08G 1/005 455/456.5 |
| 2009/0047645 A1 | 2/2009 | Dibenedetto et al. | |
| 2009/0048070 A1 | 2/2009 | Vincent et al. | |
| 2009/0094557 A1 | 4/2009 | Howard | |
| 2009/0100332 A1 | 4/2009 | Kanjilal et al. | |
| 2009/0265623 A1 | 10/2009 | Kho et al. | |
| 2010/0099539 A1 | 4/2010 | Haataja | |
| 2010/0167712 A1 | 7/2010 | Stallings et al. | |
| 2010/0187074 A1 | 7/2010 | Manni | |
| 2010/0257014 A1 | 10/2010 | Roberts et al. | |
| 2010/0313042 A1 | 12/2010 | Shuster | |
| 2011/0010704 A1 | 1/2011 | Jeon et al. | |
| 2011/0152695 A1 | 6/2011 | Granqvist et al. | |
| 2011/0218385 A1 | 9/2011 | Bolyard et al. | |
| 2011/0251822 A1 | 10/2011 | Darley et al. | |
| 2011/0252351 A1 | 10/2011 | Sikora et al. | |
| 2011/0281687 A1 | 11/2011 | Gilley et al. | |
| 2011/0283224 A1 | 11/2011 | Ramsey et al. | |
| 2011/0288381 A1 | 11/2011 | Bartholomew et al. | |
| 2011/0296312 A1 | 12/2011 | Boyer et al. | |
| 2011/0307723 A1 | 12/2011 | Cupps et al. | |
| 2012/0022336 A1 | 1/2012 | Teixeira | |
| 2012/0100895 A1 | 4/2012 | Priyantha et al. | |
| 2012/0109518 A1 | 5/2012 | Huang | |
| 2012/0116548 A1 | 5/2012 | Goree et al. | |
| 2012/0123806 A1 | 5/2012 | Schumann et al. | |
| 2012/0158289 A1 * | 6/2012 | Bernheim Brush | G06F 16/248 701/425 |
| 2012/0185268 A1 | 7/2012 | Wiesner et al. | |
| 2012/0219186 A1 | 8/2012 | Wang et al. | |
| 2012/0239173 A1 | 9/2012 | Laikari et al. | |
| 2012/0283855 A1 | 11/2012 | Hoffman et al. | |
| 2012/0289791 A1 | 11/2012 | Jain et al. | |
| 2012/0317520 A1 | 12/2012 | Lee | |
| 2013/0053990 A1 | 2/2013 | Ackland et al. | |
| 2013/0060167 A1 | 3/2013 | Dracup et al. | |
| 2013/0095459 A1 | 4/2013 | Tran | |
| 2013/0127636 A1 | 5/2013 | Aryanpur et al. | |
| 2013/0151874 A1 | 6/2013 | Parks et al. | |
| 2013/0178334 A1 | 7/2013 | Brammer | |
| 2013/0187789 A1 | 7/2013 | Lowe | |
| 2013/0190903 A1 | 7/2013 | Balakrishnan et al. | |
| 2013/0217979 A1 | 8/2013 | Blackadar et al. | |
| 2013/0225370 A1 | 8/2013 | Flynt et al. | |
| 2013/0234924 A1 | 9/2013 | Janefalkar et al. | |
| 2013/0250845 A1 | 9/2013 | Greene et al. | |
| 2013/0289932 A1 | 10/2013 | Baechler et al. | |
| 2013/0304377 A1 | 11/2013 | Van Hende | |
| 2013/0312043 A1 | 11/2013 | Stone et al. | |
| 2013/0332286 A1 | 12/2013 | Medelius et al. | |
| 2013/0345978 A1 | 12/2013 | Lush et al. | |
| 2014/0018686 A1 | 1/2014 | Medelius et al. | |
| 2014/0046223 A1 | 2/2014 | Kahn et al. | |
| 2014/0094200 A1 | 4/2014 | Schatzberg et al. | |
| 2014/0142732 A1 | 5/2014 | Karvonen | |
| 2014/0149754 A1 | 5/2014 | Silva et al. | |
| 2014/0159915 A1 | 6/2014 | Hong et al. | |
| 2014/0163927 A1 | 6/2014 | Molettiere et al. | |
| 2014/0208333 A1 | 7/2014 | Beals et al. | |
| 2014/0218281 A1 | 8/2014 | Amayeh et al. | |
| 2014/0235166 A1 | 8/2014 | Molettiere et al. | |
| 2014/0237028 A1 | 8/2014 | Messenger et al. | |
| 2014/0257533 A1 * | 9/2014 | Morris | A63B 24/00 700/91 |
| 2014/0275821 A1 | 9/2014 | Beckman | |
| 2014/0288680 A1 * | 9/2014 | Hoffman | G09B 5/02 700/91 |
| 2014/0336796 A1 | 11/2014 | Agnew | |
| 2014/0337036 A1 | 11/2014 | Haiut et al. | |
| 2014/0337450 A1 | 11/2014 | Choudhary et al. | |
| 2014/0343380 A1 | 11/2014 | Carter et al. | |
| 2014/0350883 A1 | 11/2014 | Carter et al. | |
| 2014/0365107 A1 | 12/2014 | Dutta et al. | |
| 2014/0372064 A1 | 12/2014 | Darley et al. | |
| 2015/0006617 A1 | 1/2015 | Yoo et al. | |
| 2015/0037771 A1 | 2/2015 | Kaleal, III et al. | |
| 2015/0042468 A1 | 2/2015 | White et al. | |
| 2015/0057945 A1 | 2/2015 | White et al. | |
| 2015/0113417 A1 | 4/2015 | Yuen et al. | |
| 2015/0119198 A1 | 4/2015 | Wisbey et al. | |
| 2015/0119728 A1 | 4/2015 | Blackadar et al. | |
| 2015/0127966 A1 | 5/2015 | Ma et al. | |
| 2015/0141873 A1 | 5/2015 | Fei | |
| 2015/0160026 A1 | 6/2015 | Kitchel | |
| 2015/0180842 A1 | 6/2015 | Panther | |
| 2015/0185815 A1 | 7/2015 | Debates et al. | |
| 2015/0209615 A1 | 7/2015 | Edwards | |
| 2015/0233595 A1 | 8/2015 | Fadell et al. | |
| 2015/0272483 A1 | 10/2015 | Etemad et al. | |
| 2015/0312857 A1 | 10/2015 | Kim et al. | |
| 2015/0326709 A1 | 11/2015 | Pennanen et al. | |
| 2015/0335978 A1 | 11/2015 | Syed et al. | |
| 2015/0342533 A1 | 12/2015 | Kelner | |
| 2015/0347983 A1 | 12/2015 | Jon et al. | |
| 2015/0350822 A1 | 12/2015 | Xiao et al. | |
| 2015/0362519 A1 | 12/2015 | Balakrishnan et al. | |
| 2015/0374279 A1 | 12/2015 | Takakura et al. | |
| 2015/0382150 A1 | 12/2015 | Ansermet et al. | |
| 2016/0007288 A1 | 1/2016 | Samardzija et al. | |

(56) References Cited

U.S. PATENT DOCUMENTS

| | | |
|---|---|---|
| 2016/0007934 A1 | 1/2016 | Arnold et al. |
| 2016/0023043 A1 | 1/2016 | Grundy |
| 2016/0026236 A1 | 1/2016 | Vasistha et al. |
| 2016/0034043 A1 | 2/2016 | Le Grand et al. |
| 2016/0034133 A1 | 2/2016 | Wilson et al. |
| 2016/0041593 A1 | 2/2016 | Dharawat |
| 2016/0058367 A1 | 3/2016 | Raghuram et al. |
| 2016/0058372 A1 | 3/2016 | Raghuram et al. |
| 2016/0059079 A1 | 3/2016 | Watterson |
| 2016/0072557 A1 | 3/2016 | Ahola |
| 2016/0081028 A1 | 3/2016 | Chang et al. |
| 2016/0081625 A1 | 3/2016 | Kim et al. |
| 2016/0084869 A1 | 3/2016 | Yuen et al. |
| 2016/0091980 A1 | 3/2016 | Baranski et al. |
| 2016/0104377 A1* | 4/2016 | French ............... G08G 1/0129 701/117 |
| 2016/0135698 A1 | 5/2016 | Baxi et al. |
| 2016/0143579 A1 | 5/2016 | Martikka et al. |
| 2016/0144236 A1 | 5/2016 | Ko et al. |
| 2016/0148396 A1 | 5/2016 | Bayne et al. |
| 2016/0148615 A1 | 5/2016 | Lee et al. |
| 2016/0184686 A1 | 6/2016 | Sampathkumaran |
| 2016/0209907 A1 | 7/2016 | Han et al. |
| 2016/0226945 A1 | 8/2016 | Granqvist et al. |
| 2016/0259495 A1 | 9/2016 | Butcher et al. |
| 2016/0317097 A1 | 11/2016 | Adams et al. |
| 2016/0327915 A1 | 11/2016 | Katzer et al. |
| 2016/0328991 A1 | 11/2016 | Simpson et al. |
| 2016/0346611 A1* | 12/2016 | Rowley ............... A61B 5/1118 |
| 2016/0374566 A1 | 12/2016 | Fung et al. |
| 2016/0379547 A1 | 12/2016 | Okada |
| 2017/0010677 A1 | 1/2017 | Roh et al. |
| 2017/0011089 A1 | 1/2017 | Bermudez et al. |
| 2017/0011210 A1 | 1/2017 | Cheong et al. |
| 2017/0032256 A1 | 2/2017 | Otto et al. |
| 2017/0038740 A1 | 2/2017 | Knappe et al. |
| 2017/0063475 A1 | 3/2017 | Feng |
| 2017/0065230 A1 | 3/2017 | Sinha et al. |
| 2017/0087431 A1 | 3/2017 | Syed et al. |
| 2017/0124517 A1 | 5/2017 | Martin |
| 2017/0153119 A1 | 6/2017 | Nieminen et al. |
| 2017/0153693 A1 | 6/2017 | Duale et al. |
| 2017/0154270 A1 | 6/2017 | Lindman et al. |
| 2017/0168555 A1 | 6/2017 | Munoz et al. |
| 2017/0173391 A1 | 6/2017 | Wiebe et al. |
| 2017/0232294 A1 | 8/2017 | Kruger et al. |
| 2017/0262699 A1 | 9/2017 | White et al. |
| 2017/0266494 A1* | 9/2017 | Crankson ............ A63B 24/0062 |
| 2017/0316182 A1 | 11/2017 | Blackadar et al. |
| 2017/0340221 A1 | 11/2017 | Cronin et al. |
| 2018/0015329 A1 | 1/2018 | Burich et al. |
| 2018/0108323 A1 | 4/2018 | Lindman et al. |
| 2018/0193695 A1 | 7/2018 | Lee |
| 2018/0345077 A1 | 12/2018 | Blahnik et al. |
| 2019/0025928 A1 | 1/2019 | Pantelopoulos et al. |
| 2019/0056777 A1 | 2/2019 | Munoz et al. |
| 2019/0367143 A1 | 12/2019 | Sinclair et al. |

FOREIGN PATENT DOCUMENTS

| | | |
|---|---|---|
| CN | 102495756 A | 6/2012 |
| CN | 103309428 A | 9/2013 |
| CN | 103631359 A | 3/2014 |
| CN | 204121706 U | 1/2015 |
| CN | 104680046 A1 | 6/2015 |
| CN | 105242779 A1 | 1/2016 |
| CN | 106062661 A | 10/2016 |
| CN | 106604369 A | 4/2017 |
| CN | 108052272 A | 5/2018 |
| CN | 103154954 B | 6/2018 |
| CN | 108377264 A | 8/2018 |
| CN | 108983873 A | 12/2018 |
| EP | 1755098 A2 | 2/2007 |
| EP | 2096820 A1 | 9/2009 |
| EP | 2107837 A1 | 10/2009 |
| EP | 2172249 A2 | 4/2010 |
| EP | 2770454 A1 | 8/2014 |
| EP | 2703945 A2 | 3/2015 |
| EP | 2849473 A1 | 3/2015 |
| EP | 2910901 A1 | 8/2015 |
| EP | 3023859 A1 | 5/2016 |
| EP | 3361370 A | 8/2018 |
| FI | 126911 B | 2/2017 |
| GB | 2404593 A | 2/2005 |
| GB | 2425180 A | 10/2006 |
| GB | 2513585 A | 11/2014 |
| GB | 2530196 A | 3/2016 |
| GB | 2537423 A | 10/2016 |
| GB | 2541234 A | 2/2017 |
| GB | 2555107 A | 4/2018 |
| KR | 20110070049 A | 6/2011 |
| KR | 101500662 B1 | 3/2015 |
| SE | 528295 C2 | 10/2006 |
| TW | 201706840 A | 2/2017 |
| TW | I598076 A | 9/2018 |
| WO | WO02054157 A1 | 7/2002 |
| WO | WO2010083562 A1 | 7/2010 |
| WO | WO2010144720 A1 | 12/2010 |
| WO | WO2011061412 A1 | 5/2011 |
| WO | WO2011123932 A1 | 10/2011 |
| WO | WO2012037637 A1 | 3/2012 |
| WO | WO2012115943 A1 | 8/2012 |
| WO | WO2012141827 A2 | 10/2012 |
| WO | WO2013091135 A1 | 6/2013 |
| WO | WO2013121325 A2 | 8/2013 |
| WO | WO2014118767 A1 | 8/2014 |
| WO | WO2014144258 A2 | 9/2014 |
| WO | WO2014193672 A1 | 12/2014 |
| WO | WO2014209697 A1 | 12/2014 |
| WO | WO2014182162 A3 | 6/2015 |
| WO | WO2015087164 A1 | 6/2015 |
| WO | WO2015131065 A1 | 9/2015 |
| WO | WO2016022203 A1 | 2/2016 |
| WO | WO2017011818 A1 | 1/2017 |
| WO | WO2018217348 A1 | 11/2018 |
| WO | WO2018222936 A1 | 12/2018 |

OTHER PUBLICATIONS

Qualcomm Snapdragon Wear 3100 Platform Supports New Ultra-Low Power System Architecture For Next Generation Smartwatches. Qualcomm Technologies, Inc., Sep. 10, 2018, Retrieved on May 28, 2020 from: <https://www.qualcomm.com/news/releases/2018/09/10/qualcomm-snapdragon-wear-3100-platform-supports sections "Snapdragon Wear 3100 Based Smartwatches Aim to Enrich the User Experience" pp. 3-4.

CNET: Dec. 11, 2017, "Apple watch can now sync with a treadmill", youtube.com, [online], Available from: https://www.youtube.com/watch?v=7RvMC3wFDME [ Accessed Nov. 19, 2020].

Sheta et al: Packet scheduling in LTE mobile network. International Journal of Scientific & Engineering Research, Jun. 2013, vol. 4, Issue 6.

Sieber et al.: Embedded systems in the Poseidon MK6 rebreather. Intelligent Solutions in Embedded Systems. 2009. pp. 37-42.

Cash: A guide to GPS and route plotting for cyclists. 2018. www.cyclinguk.org/article/guide-gps-and-route-plotting-cyclists.

* cited by examiner

THEMATIC MAP BASED ROUTE OPTIMIZATION

FIELD

The present application relates to the field of device usability and safety.

BACKGROUND

A user interface, UI, enables a user to interact with a device, such as, for example, a car, a smartphone, an automated banking device or an aircraft control system. Different user interfaces are appropriate for different purposes, for example, where the user uses the device to perform actions that set persons at risk, the quality and quantity of information presented to the user when interacting with the user interface must be sufficient to enable use of the device safely, while not overloading the user with unnecessary information.

User interfaces may be based on presenting information to the user, and receiving inputs from the user. Information may be presented using an output device such as a display, for example an organic light-emitting diode, OLED, display. Inputs may be received from the user via various input devices, such as touchscreen displays, push buttons, microphones arranged to capture the user's speech and/or levers the user can pull.

A traditional user interface of a wristwatch comprises a long and a short arm, which rotate over a watch dial to indicate the time of day. Digital wrist watches may comprise, for example, a liquid crystal display, LCD, type display indicating the time of day numerically.

A smart watch may comprise a touchscreen, such that the display portion of the touchscreen acts as an output device of the user interface and the touch sensitive portion of the touchscreen acts as an input device of the user interface. Using a smart watch presents challenges, since useful applications tend to require larger screens to present a useful quantity of information using a font large enough, that users can read it without magnifying devices.

A personal device, such as a smart watch or other kind of personal device, may keep track of a route that the user traverses, for example while jogging or performing another kind of activity. The route may be compiled in the personal device based, at least in part, on keeping track of a geographical location of the personal device.

SUMMARY OF THE INVENTION

The invention is defined by the features of the independent claims. Some specific embodiments are defined in the dependent claims.

According to a first aspect of the present invention, there is provided an apparatus comprising at least one processing core, at least one memory including computer program code, the at least one memory and the computer program code being configured to, with the at least one processing core, cause the apparatus at least to determine a route based at least partly on a thematic map database and a current location of the apparatus, present the determined route as a suggested route to a first user, and responsive to the first user approving the suggested route, initiate an activity session based on the suggested route.

Various embodiments of the first aspect may comprise at least one feature from the following bulleted list:

- the thematic map database comprises a heat map
- the thematic map database associates at least one of the following with geographic locations: past indications of activity sessions, traffic density, crime density, avalanche risk density, and past indications of photography
- at least one of the past indications of activity sessions and the past indications of photography have been made by a plurality of users
- the at least one memory and the computer program code are configured to, with the at least one processing core, cause the apparatus to determine the route based at least partly on at least one of the following: a season of the year, a time of day, user settings of the first user, history information of the first user, elevation information and a location of the apparatus
- the user settings of the first user comprise settings relating to at least one of the following: a desired energy consumption of a physical exercise session, a desired cardiovascular effect of the physical exercise session, a desired oxygen consumption effect of the physical exercise session, a desired EPOC effect of the physical exercise session, a desired recovery time length of the physical exercise session, and an indication the user wishes the route to be conveniently interruptable
- the energy consumption comprises an increased energy consumption in the user's body, the increase being due to the physical exercise comprised in the physical exercise session
- the apparatus is configured to determine at least two routes, and to present at least a second determined route for the user to choose from
- the at least one memory and the computer program code are configured to, with the at least one processing core, cause the apparatus to determine the route at least partly by transmitting a query to a thematic map database server, the query comprising an indication of the current location of the apparatus
- at least one memory and the computer program code are configured to, with the at least one processing core, cause the apparatus to display the suggested route on a display comprised in the apparatus
- the at least one memory and the computer program code are configured to, with the at least one processing core, cause the apparatus to determine the first user has approved the suggested route based on determining, based at least partly on changes in the location of the apparatus, that the user is following the suggested route.

According to a second aspect of the present invention, there is provided a method comprising determining a route based at least partly on a thematic map database and a current location of an apparatus, presenting the determined route as a suggested route to a first user, and responsive to the first user approving the suggested route, initiating an activity session based on the suggested route.

Various embodiments of the second aspect may comprise at least one feature corresponding to a feature from the preceding bulleted list laid out in connection with the first aspect.

According to a third aspect of the present invention, there is provided an apparatus comprising means for determining a route based at least partly on a thematic map database and a current location of the apparatus, means for presenting the determined route as a suggested route to a first user, and means for initiating an activity session based on the suggested route responsive to the first user approving the suggested route.

According to a fourth aspect of the present invention, there is provided a non-transitory computer readable medium having stored thereon a set of computer readable instructions that, when executed by at least one processor, cause an apparatus to at least determine a route based at least partly on a thematic map database and a current location of the apparatus, present the determined route as a suggested route to a first user, and responsive to the first user approving the suggested route, initiate an activity session based on the suggested route.

According to a sixth aspect of the present invention, there is provided a method comprising receiving an indication of a location of a device, determining a route based at least partly on a thematic map database and the location of the device, and transmitting to the device an indication of the determined route. More than one route may be determined, and where more than one route is determined, an indication concerning at least two routes may be transmitted to the device. The method according to the sixth aspect may be performed in a server, for example.

According to a sixth aspect of the present invention, there is provided a computer program configured to cause a method in accordance with the second or fifth aspect to be performed.

EMBODIMENTS

A thematic map database, for example a heat map, may be compiled to cover a geographic area. Users may engage in activity sessions while in the geographic area. Activity types of such activity sessions may include jogging, swimming and cycling, for example. When a user wishes to engage in an activity session of his own, his device may determine a route for this activity session based at least in part on the thematic map database. Determining the route may comprise designing the route, optionally based partly on user settings, based on where other users have engaged in activity sessions of the same type in the past. For example, a jogging route may be determined based, at least partly, on indications where other users have jogged in the past. Route determination may be partly based on further considerations as well, as will be laid out below.

Figure 1A:
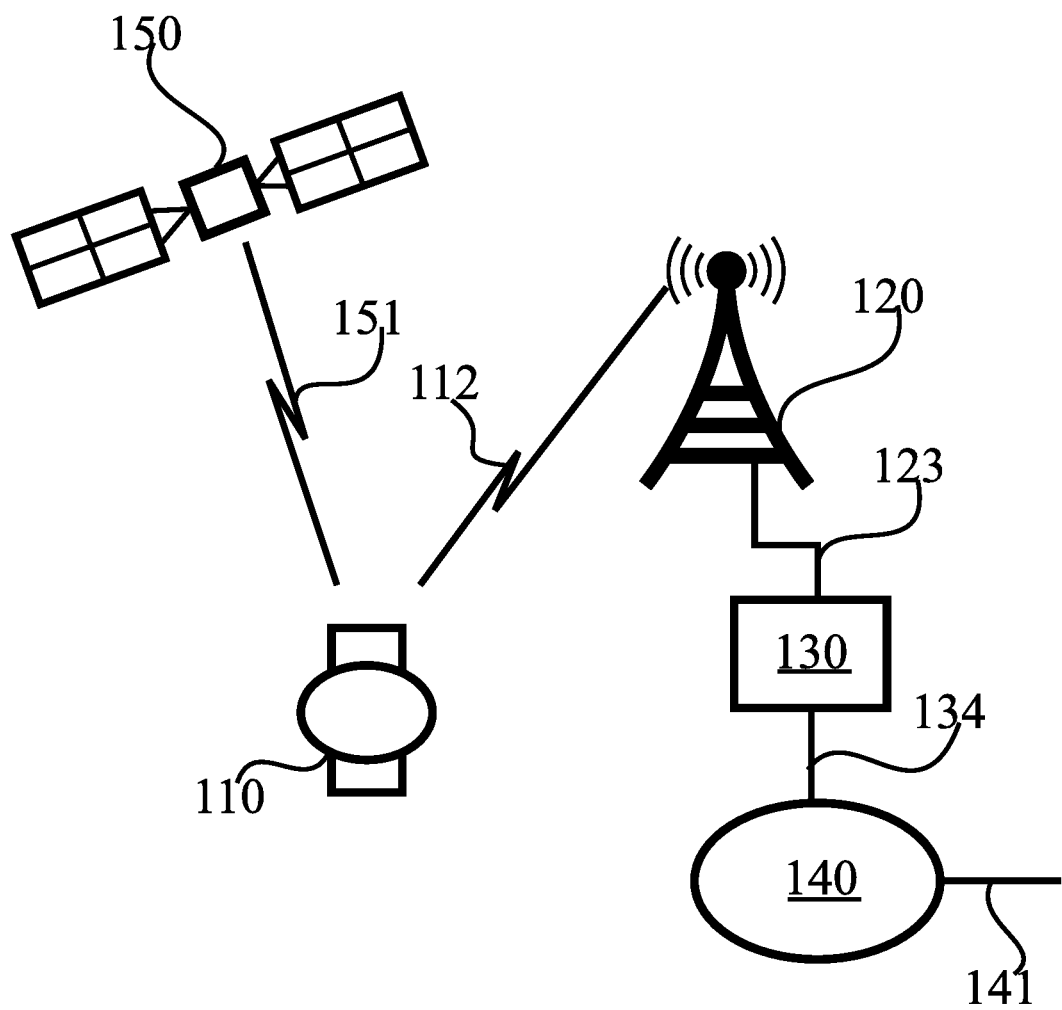
FIG. 1A illustrates a system in accordance with at least some embodiments of the present invention.

FIG. 1A illustrates a system in accordance with at least some embodiments of the present invention. The system comprises device 110, which may comprise, for example, a smart watch, digital watch, smartphone, phablet device, tablet device, or another type of suitable device. Device 110 comprises a display, which may comprise a touchscreen display, for example. The display may be limited in size. Device 110 may be powered, for example, by a rechargeable battery. An example of a limited-size display is a display worn on a wrist.

Device 110 may be communicatively coupled with a communications network. For example, in FIG. 1A device 110 is coupled, via wireless link 112, with base station 120. Base station 120 may comprise a cellular or non-cellular base station, wherein a non-cellular base station may be referred to as an access point. Examples of cellular technologies include wideband code division multiple access, WCDMA, and long term evolution, LTE, while examples of non-cellular technologies include wireless local area network, WLAN, and worldwide interoperability for microwave access, WiMAX. Base station 120 may be coupled with network node 130 via connection 123. Connection 123 may be a wire-line connection, for example. Network node 130 may comprise, for example, a controller or gateway device. Network node 130 may interface, via connection 134, with network 140, which may comprise, for example, the Internet or a corporate network. Network 140 may be coupled with further networks via connection 141. In some embodiments, device 110 is not configured to couple with base station 120.

Device 110 may be configured to receive, from satellite constellation 150, satellite positioning information via satellite link 151. The satellite constellation may comprise, for example the global positioning system, GPS, or the Galileo constellation. Satellite constellation 150 may comprise more than one satellite, although only one satellite is illustrated in FIG. 1A for the same of clarity. Likewise, receiving the positioning information over satellite link 151 may comprise receiving data from more than one satellite.

Alternatively or additionally to receiving data from a satellite constellation, device 110 may obtain positioning information by interacting with a network in which base station 120 is comprised. For example, cellular networks may employ various ways to position a device, such as trilateration, multilateration or positioning based on an identity of a base station with which attachment is possible or ongoing. Likewise a non-cellular base station, or access point, may know its own location and provide it to device 110, enabling device 110 to position itself within communication range of this access point.

Device 110 may be configured to obtain a current time from satellite constellation 150, base station 120 or by requesting it from a user, for example. Once device 110 has the current time and an estimate of its location, device 110 may consult a look-up table, for example, to determine a time remaining until sunset or sunrise, for example. Device 110 may likewise gain knowledge of the time of year.

Device 110 may be configured to provide an activity session. An activity session may be associated with an activity type. Examples of activity types include rowing, paddling, cycling, jogging, walking, hunting and paragliding. In a simplest form, an activity session may comprise device 110 displaying a map of the surroundings, and a route on the map that relates to the activity session. Device 110 may be configured to display, on the route, an indication where along the route the user is currently located, enabling the user to see the place along the route where his jog, for example, is at the moment progressing.

An activity session in device 110 may enhance a utility a user can obtain from the activity, for example, where the activity involves movement outdoors, the activity session may provide a recording of the activity session. An activity session in device 110 may, in some embodiments, provide the user with contextual information during the activity session. Such contextual information may comprise, for example, locally relevant weather information, received via base station 120, for example. Such contextual information may comprise at least one of the following: a rain warning, a temperature warning, an indication of time remaining before sunset, an indication of a nearby service that is relevant to the activity, a security warning, an indication of nearby users and an indication of a nearby location where several other users have taken photographs. Where the contextual information comprises a security warning, the warning may comprise a security route, determined in a way that enables the user to avoid danger. For example, in case of a chemical leak, the security route may comprise a route that leads indoors or to public transport. Device 110 may determine a security route, or device 110 may receive the security route, at least in part, from a network. The security route may be determined using existing roads, pathways and other transit routes that are known to the entity determining the security route. Transit routes may be known from a public mapping service, for example.

A recording may comprise information on at least one of the following: a route taken during the activity session, a metabolic rate or metabolic effect of the activity session, a time the activity session lasted, a quantity of energy consumed during the activity session, a sound recording obtained during the activity session and an elevation map along the length of the route taken during the activity session. A route may be determined based on positioning information, for example. Metabolic effect and consumed energy may be determined, at least partly, based on information concerning the user that device 110 has access to. A recording may be stored in device 110, an auxiliary device, or in a server or data cloud storage service. A recording stored in a server or cloud may be encrypted prior to transmission to the server or cloud, to protect privacy of the user.

An activity session may have access to a backhaul communications link to provide indications relating to the ongoing activity. For example, search and rescue services may be given access to information on joggers in a certain area of a forest, to enable their rescue if a chemical leak, for example, makes the forest unsafe for humans. In some embodiments, routes relating to activity sessions are provided to a cloud service for storage when the activity sessions start, to enable searching for missing persons along the route the persons were planning to take.

The user may initiate an activity session by interacting with a user interface of device 110, for example. Where device 110 has s small form factor, the user interface may be implemented over a limited user interaction capability, such as, for example, a small screen, small touchscreen, and/or limited number of push buttons. A limited user interaction capability may make it arduous for the user to perform complicated interactions with device 110, which makes it less likely the user will choose to interact with device 110. Therefore, it is of interest to simplify the interaction between device 110 and the user, to make it easier for the user to complete the interaction, and thus more likely the user will perform the interaction.

Device 110 may provide to the thematic map database an indication relating to the activity session, to enhance the thematic map database further. Such indications may be anonymized prior to sending to the database, both to protect the user's privacy and/or to comply with local legislation. Such indications may comprise, for example, information on a determined route and a corresponding activity type.

In general, a thematic map database may associate at least one form of data with a geographic location. For example, the thematic map database may associate past indications of activity sessions with geographic locations, for example to enable mapping areas where activity sessions of a given activity type have been performed. Areas may be mapped as to the intensity, or frequency, of past indications of activity session and type. Thus a first area of a lake may be associated with frequent rowing, and another area of the same lake with less frequent, but still non-zero, rowing. Such a frequency may be referred to as an intensity, and the thematic map database may, in general, associate activity type intensities with locations. Alternatively to intensities, the thematic map database may simply associate, whether an activity session of a given activity type has in the past been performed in a geographic location. Additionally or alternatively, a traffic density may be associated with the geographic locations. Traffic density may comprise pedestrian or vehicular traffic density, for example. Walking or jogging may be less pleasant, or less healthy, in areas with a high vehicular traffic density due to exhaust fumes, wherefore a route relating to an activity session with such type may be determined in a way that avoids such high-traffic density areas. Likewise, additionally or alternatively, crime density may be mapped, and employed in route determination to avoid high-crime areas. Avalanche risk density, obtained from meteorological services, may similarly be used to route ski activity sessions in safe areas. In some embodiments, places where many users have taken photographs may be used in routing, such that routes are determined to visit frequently photographed locations, since such locations are likely to be beautiful and inspiring.

In some embodiments, the user may have indicated in user settings that he wishes to engage in a certain type of activity session, wherein such indications may be taken into account when determining the route for the activity session. The settings may be taken into account, for example, by designing the route so that performing the activity session along the route causes an increase in energy consumption in the user that is approximately in line with what the user has requested in the settings. Alternatively or additionally, a cardiovascular effect of the activity session may be tuned to be in line with a user setting by designing the route in a suitable way. Likewise the user may specify a desired effect on oxygen consumption, EPOC effect and/or a recovery time length after the activity session. EPOC refers to excess post-exercise oxygen consumption, sometimes known colloquially as afterburn.

The route may be determined in such a way as to be interruptable. For example, where the activity comprises cycling, the route may come close to the starting and ending location close to a midpoint of the route, to enable the user to cut the route short. The user may specify in user settings he wishes to engage in an interruptable route, or interruptability may be a default setting that is attempted to comply with, where possible.

A level of physical exertion, in terms of energy consumption, oxygen consumption, cardiovascular effect, EPOC or recovery time length, the route causes in the user may be modified by determining elevation changes along the route.

Where the user wishes a light activity session, the route may be determined as relatively flat, and where the user wishes for a strenuous activity session, the route may be determined in a way that it has more elevation changes. Using the thematic map database in connection with elevation data in this sense may comprise, for example, determining the route based on elevation changes to match the desired strenuousness, in an area which the thematic map database indicates that activity sessions of a corresponding type have been conducted in the past. In general, the user settings may be employed in determining the route after a suitable area for the route has been identifier using the thematic map database.

A time of year and/or a time of day may be employed in either the thematic map database or in the determining of the route. For example, the thematic map database may comprise data collected at different times of year, for example a same location may be associated with frequent jogging in summertime and frequent skiing during the winter months. Thus, the database may return a jogging route in the location in case the query is made in the summer, and the database may return a skiing route in the location in case the query is made in the winter. Alternatively or in addition, device 110 may select activity types consistent with the time of year, or time of day, from the set of activity types returned from the database when determining the predicted user activity type. Device 110 may perform this task in embodiments where the database doesn't collect statistics separately according to time of year or day, for example. As a specific example, local residents may consider a certain location as safe during the day but unsafe after dark. In such a situation, a user requesting a jogging route could be routed to this location if the request is made in the daytime, but routed elsewhere if the request is made after dark.

In general, the thematic map database may be comprised in a server or cloud device, or it may be downloaded, at least in part, to device 110 or an auxiliary device, for offline use. An auxiliary device is described below in connection with FIG. 1B. While described herein primarily as a route determination method performed by device 110, in various embodiments of the invention the route determination may take place in another device, such as the auxiliary device or a cloud computing device, for example. The user may have an account in a cloud computing service, where his information may be stored and he may request for a route to be determined and furnished to his device, such as, for example, device 110.

Responsive to the user approving, implicitly or explicitly, a suggested route, an activity session based on the approved suggested route may be initiated.

More than one route may be determined, such that at least one of the determined routes is presented to the user as a suggested route. For example, two routes may be determined that match requirements defined by the user, and these two routes may then be presented as suggested routes, with information concerning each route presented to the user as well. For example, energy consumption, estimated time to completion and/or length of a route may be presented to assist the user in making a selection. Energy consumption, estimated time to completion and/or other suitable information may be determined, at least partly, on the elevation information.

Information may be presented also, or alternatively, concerning segments of any suggested route, to enable the user to construct his route from interconnected segments.

In some embodiments, the user needn't explicitly select a suggested route, rather, the device may deduce from the way positioning information changes, which route the user is following. As a response, any other suggested routes may be removed from the display to reduce clutter. In case the user deviates from the route, the device may notice this from the positioning information, and responsively determine an alternative route for the user, which may again be displayed. Thus movement of the user may cause, via the positioning information, an approval of a suggested route and/or a new determination of a new suggested route in case of deviation from a previously approved route. Such a new suggested route may be determined from the current location of the device to the same end point as the originally approved route. Such an end point may comprise the start point of the route, or, alternatively, another point input by the user. Remaining time, energy consumption and/or other information may be presented concerning the new suggested route.

Figure 1B:
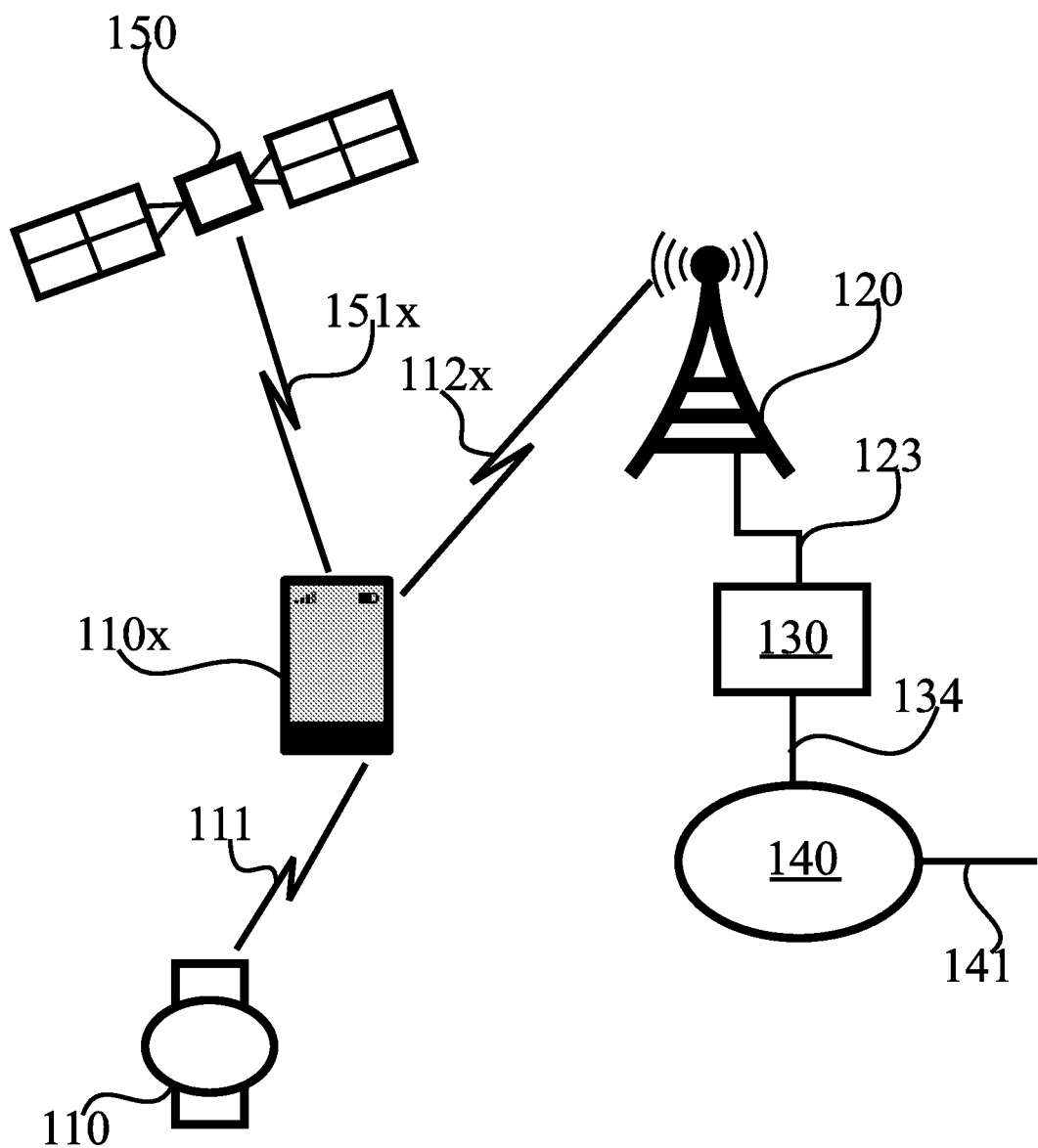
FIG. 1B illustrates a system in accordance with at least some embodiments of the present invention.

FIG. 1B illustrates a system in accordance with at least some embodiments of the present invention. Like numbering denotes like structure as in FIG. 1A. FIG. 1B embodiments comprise an auxiliary device 110x.

Device 110 may be communicatively coupled, for example communicatively paired, with an auxiliary device 110x. The communicative coupling, or pairing, is illustrated in FIG. 1A as interface 111, which may be wireless, as illustrated, or wire-line, depending on the embodiment. Auxiliary device 110x may comprise a smartphone, tablet computer or other computing device, for example. Auxiliary device 110x may comprise a device that the owner of device 110 uses to consume media, communicate or interact with applications. Auxiliary device 110x may be furnished with a larger display screen than device 110, which may make auxiliary device 110x preferable to the user when a complex interaction with an application is needed, as a larger screen enables a more detailed rendering of interaction options. In some embodiments, such as those illustrated in FIG. 1A, auxiliary device 110x is absent.

In some embodiments, where auxiliary device 100x is present, device 110 is configured to use connectivity capability of auxiliary device 110x. For example, device 110 may access a network via auxiliary device 110x. In these embodiments, device 110 need not be furnished with connectivity toward base station 120, for example, since device 110 may access network resources via interface 111 and a connection auxiliary device 110x has with base station 120. Such a connection is illustrated in FIG. 1B as connection 112x. For example, device 110 may comprise a smart watch and auxiliary device 110x may comprise a smartphone, which may have connectivity to cellular and/or non-cellular data networks. Likewise, in some embodiments device 110 may receive satellite positioning information, or positioning information derived therefrom, via auxiliary device 110x where device 110 lacks a satellite positioning receiver of its own. A satellite connection of auxiliary device 151x is illustrated in FIG. 1B as connection 151X.

In some embodiments, device 110 may have some connectivity and be configured to use both that and connectivity provided by auxiliary device 110x. For example, device 110 may comprise a satellite receiver enabling device 110 to obtain satellite positioning information directly from satellite constellation 150. Device 110 may then obtain network connectivity to base station 120 via auxiliary device 110x. For example, device 110 may transmit a query to the thematic map database via auxiliary device 110x. In some embodiments, device 110 is configured to request, and responsively to receive, sensor information from auxiliary device 110x. Such sensor information may comprise acceleration sensor information, for example. In general, processing, such as route determination and/or communication processing, may be distributed in a suitable way between device 110, auxiliary device 110x and/or a cloud computing service.

Figure 2A:
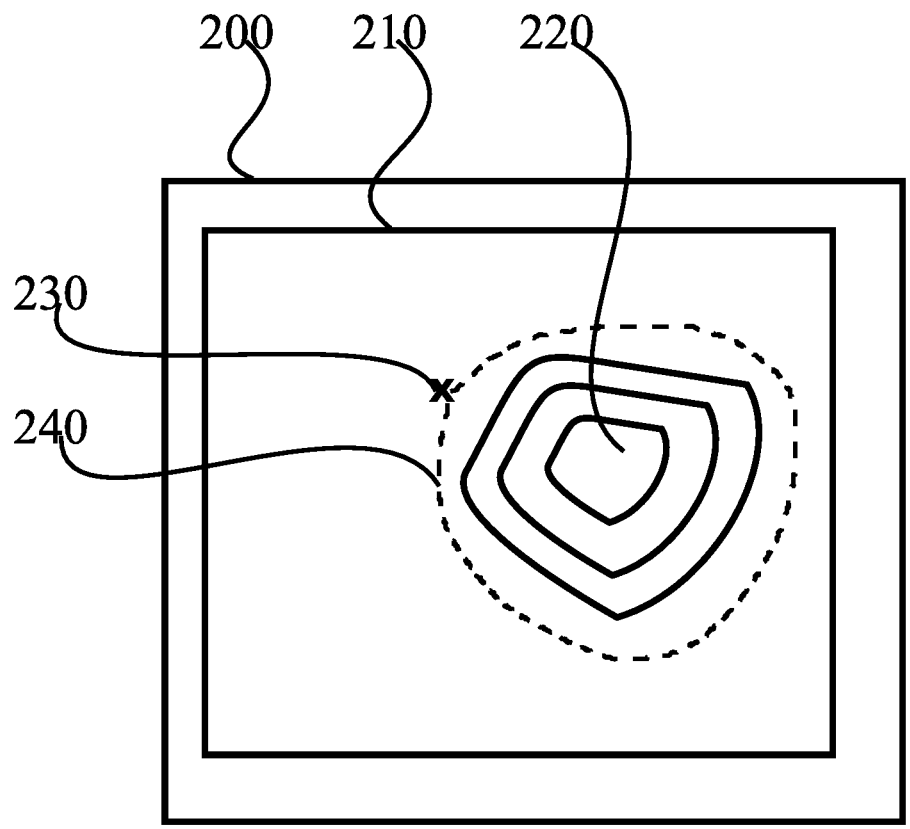
FIG. 2A illustrates an example user interface in accordance with at least some embodiments of the present invention.

FIG. 2A illustrates an example user interface in accordance with at least some embodiments of the present invention. The user interface may be comprised in device 110 of FIG. 1A or FIG. 1B, for example. Display 200 is configured to provide a user interface display to the user. Display area 210 provides an application level display to the user. In application level display 210 is comprised map 220, which may display, for example, terrain and/or elevation information. In the illustrated example, a hill is displayed in the map 220.

A start point 230 is illustrated in the user interface, as is a route 240, which is indicated with a dashed line. In this example, the route may be traversed twice to obtain the physical exercise effect the user wants. The route proceeds along a relatively constant elevation around the hill, and when traversed twice provides an opportunity to interrupt the activity session halfway through, as the user passes start point 230. To interrupt the session, the user can simply stop at start point 230 instead of beginning a second lap along the route. In this example the area of map 220 may be indicated in the thematic map database as being associated with past activity sessions of a corresponding, or indeed same, activity type as the session the user selects. The route may be determined, in part, based on mapping information obtained from a mapping service, such as a proprietary service, HERE maps or Google maps, for example. Elevation information may be obtained from the same, or similar, service.

Figure 2B:
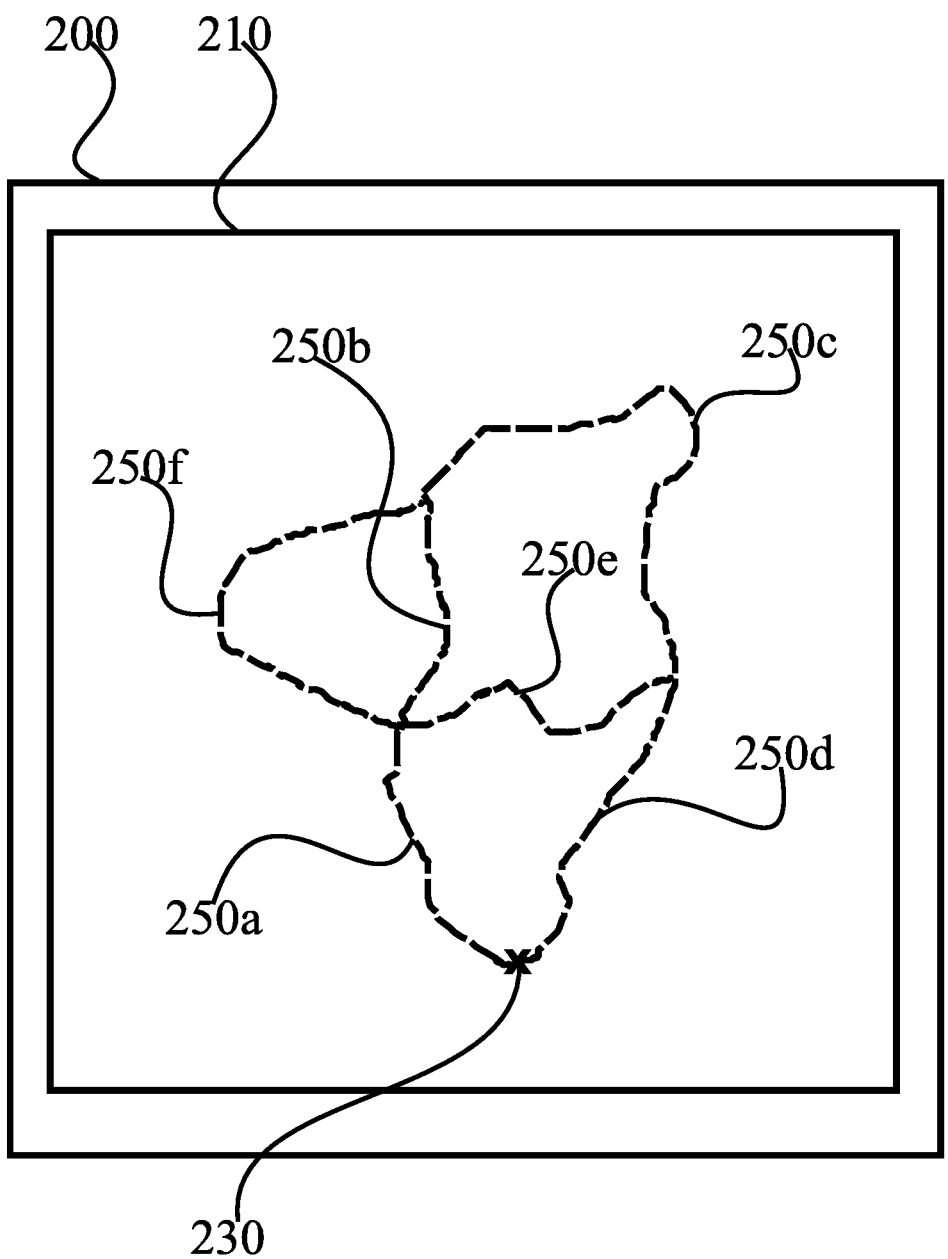
FIG. 2B illustrates a second example of a user interface in accordance with at least some embodiments of the present invention.

FIG. 2B illustrates a second example of a user interface in accordance with at least some embodiments of the present invention. Like numbering denotes like elements as in FIG. 2A. In FIG. 2B, a route planning view is presented in application level display area 210. The route planning view displays a route segment network which comprises segment 250a, segment 250b, segment 250c, segment 250d, segment 250e, and segment 250f. The user can complete a closed route from and to start point 230 via various combinatorial options. For example, a first option comprises segments 250a, 250b, 250c and 250d. For example, a second option comprises segments 250a, 250b, 250c, in that order, followed by segments 250e and 250a, in that order. The segments may be obtained based at least partly on a local map and/or a thematic map database, for example.

The user may be presented with information concerning route options, for example for the first option, an estimated energy consumption associated with an activity session along the route defined by the first option, and likewise for the second option. The user may, explicitly or implicitly, select one of the presented options, and along the route deviate therefrom to use a different set of route segments. For example, a user setting on along the first option, may decide to shorten the activity session by taking segments 250e and 250d back to the start point 230. Alternatively, the user may decide to lengthen the session by taking, in the first option, segment 250f instead of segment 250b.

In some embodiments, information is presented separately concerning route segments, to enable the user to design a route with greater precision. For example, an energy consumption associated with segment 250a, when used as a route segment in an activity session of a given type, may be presented. Likewise, other physiological effects, such as EPOC or oxygen consumption, may be presented in addition to, or alternatively to, the energy consumption.

Figure 2C:
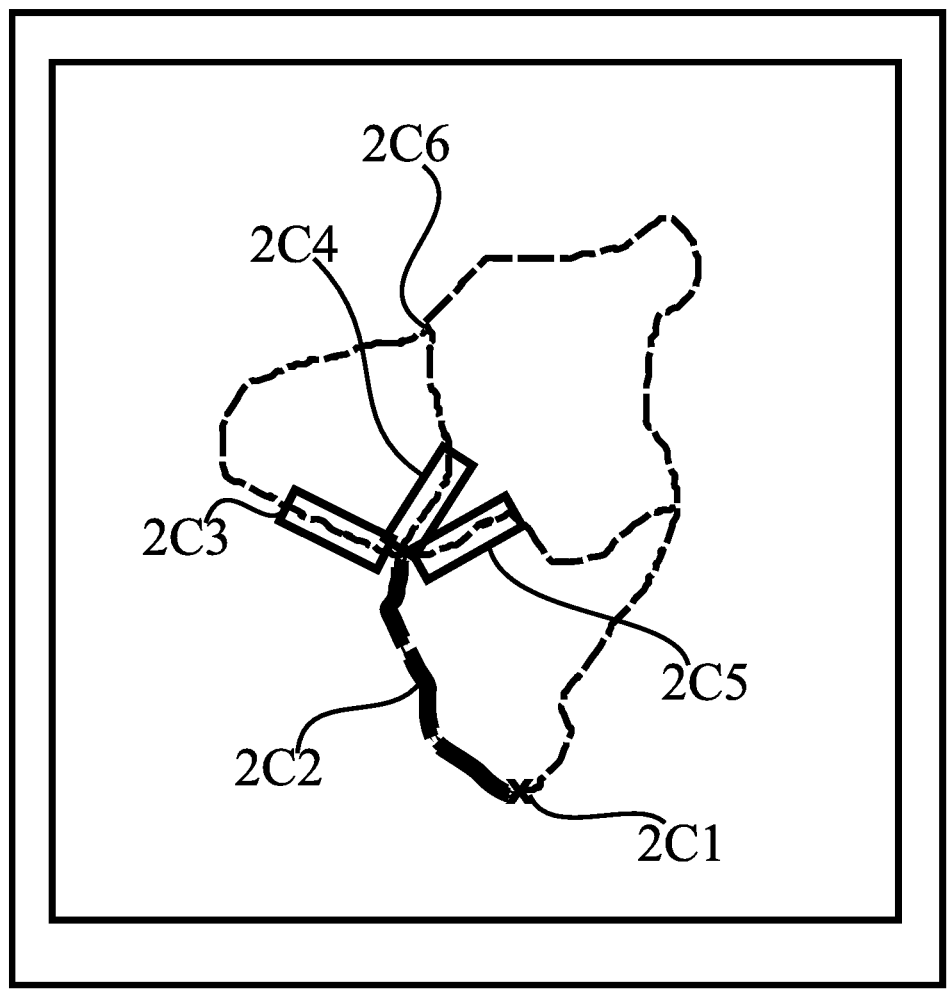
FIG. 2C illustrates a third example of a user interface in accordance with at least some embodiments of the present invention.

FIG. 2C illustrates a third example of a user interface in accordance with at least some embodiments of the present invention. The route segments of the third example may be determined from a thematic map database, such as a heat map, or a mapping application, for example. In the third example, a session begins at start point 2C1, where device 110 may be positioned using a positioning capability of the device, for example. Initially, the device is not given a route, rather, the device may use an exercise history of the user together with the start point 2C1 location to predict a route. For example, the device may assume the user intends to repeat an earlier activity session which began at this start point, or to perform a similar session to earlier sessions. The user may accept the predicted route, or, alternatively, the use may simply start the activity session along the predicted route or another route. The device may determine which route segment the user chooses from observing how positioning information of the device changes. In other words, user interaction with device 110 is not needed to enable device 110 to determine which route segment is the first one along the actual route. In some embodiments, the device does not offer an initial predicted route, rather, the user may simply begin his session, e.g. jogging or walking. The predicted route will then be initiated based on a determination concerning which route segment will be first in the actual complete route, this determination being based on positioning information of the device.

In the example illustrated in FIG. 2C, the user has selected route segment 2C2 as the first route segment of his actual route in the activity session. The device tracks the user's progress along route segment 2C2 as the activity session progresses. Once the device is able to determine route segment 2C2 has been selected, the predicted route may be updated such that it begins with route segment 2C2, in case it originally started with a different route segment. As the user approaches the end of route segment 2C2, the situation illustrated in 2C2 takes place. Route segment 2C2 is then an already traversed section of the actual route, and the intersection at the end of segment 2C2 presents three alternatives for continuing the route.

For the intersection at the end of route segment 2C2, device 110 presents three options to the user: 2C3, 2C4 and 2C5, corresponding to respective route segments which connect with route segment 2C2 at the intersection. Each of these options is labelled with information usable to the user in selecting from among the options. In detail, the labels indicate at least one of: a total route length obtainable via the respective sub-route, a total exercise session duration obtainable via the respective sub-route, a speed obtainable via the respective sub-route and a metabolic effect obtainable via the respective sub-route. A sub-route is, in general, a section of a complete actual route of an activity session that excludes the already traversed part of the actual route. Each of the options in the intersection corresponds to at least one sub-route.

In detail, associated with option 2C4, for example, are plural sub-routes since after choosing option 2C4 at the intersection, the user will be presented with a new choice at intersection 2C6, whether to turn left or right. Thus option 2C4 may be labelled with information relating to the sub-routes accessible via this option.

Device 110 may be configured to compile the labelled options based on the exercise history of a user. For example, where the user has often completed activity sessions of a certain length, device 110 may present as labelled options a subset of the possible sub-routes, such that the presented labelled options correspond to a range of total route lengths (or durations, or metabolic effects) which spans the typical activity session of the user, with also slightly shorter and slightly longer options included in the range. Thus labels corresponding to sub-routes which do not correspond at all to normal activity sessions of the user need not be presented in the view. In other words, the device may be configured to present to the user labelled options corresponding to the predicted route, and variations of the predicted route. Alternatively to predicting the route length or other target(s), the user may provide these targets, to guide the prediction of the route.

Once the user selects one of the options, the device 110 may once more determine based on positioning the device, which option the user has chosen. In other words, the user need not explicitly select any one of the options 2C3, 2C4 or 2C5 on the user interface. Once the user then arrives at a next intersection, for example 2C6, the device may once more present labelled options corresponding to activity sessions completable via respective sub-routes from this intersection. Also, the predicted route is again updated to include the route segment between the intersection at the end of segment 2C2 and intersection 2C6 as an already traversed section of the overall route, for example.

Device 110 may be configured to determine the predicted route based at least partly on at least one of the following: a thematic map database, a season of the year, a time of day, user settings of the user, history information of the user, elevation information and a location of the apparatus. User settings of the user may comprise settings relating to at least one of the following: a desired energy consumption of a physical exercise session, a desired cardiovascular effect of the physical exercise session, a desired oxygen consumption effect of the physical exercise session, a desired EPOC effect of the physical exercise session, a desired recovery time length of the physical exercise session, and an indication the user wishes the route to be conveniently interruptible.

Figure 3:
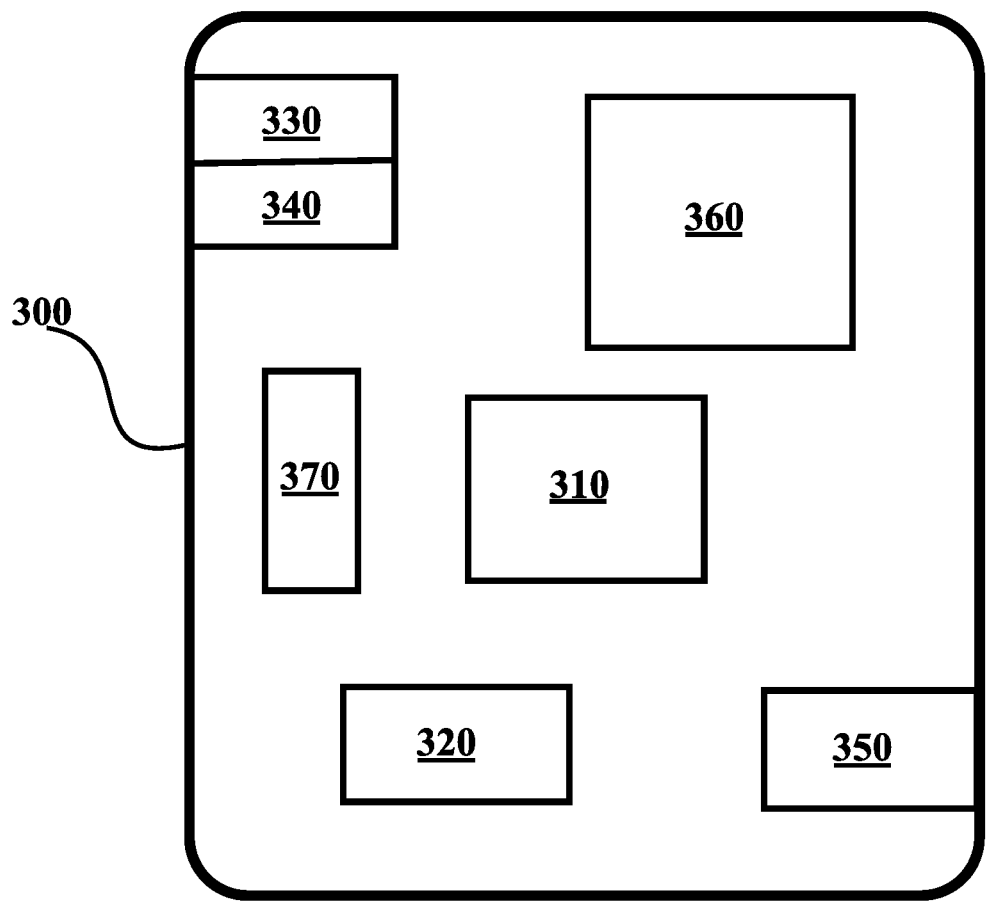
FIG. 3 illustrates an example apparatus capable of supporting at least some embodiments of the present invention.

FIG. 3 illustrates an example apparatus capable of supporting at least some embodiments of the present invention. Illustrated is device 300, which may comprise, for example, a mobile communication device such as device 110 of FIG. 1A or FIG. 1B. Device 330 may alternatively or additionally correspond to auxiliary device 110x of FIG. 1B. Comprised in device 300 is processor 310, which may comprise, for example, a single- or multi-core processor wherein a single-core processor comprises one processing core and a multi-core processor comprises more than one processing core. Processor 310 may comprise more than one processor. A processing core may comprise, for example, a Cortex-A8 processing core manufactured by ARM Holdings or a Steamroller processing core produced by Advanced Micro Devices Corporation. Processor 310 may comprise at least one Qualcomm Snapdragon and/or Intel Atom processor. Processor 310 may comprise at least one application-specific integrated circuit, ASIC. Processor 310 may comprise at least one field-programmable gate array, FPGA. Processor 310 may be means for performing method steps in device 300. Processor 310 may be configured, at least in part by computer instructions, to perform actions.

Device 300 may comprise memory 320. Memory 320 may comprise random-access memory and/or permanent memory. Memory 320 may comprise at least one RAM chip. Memory 320 may comprise solid-state, magnetic, optical and/or holographic memory, for example. Memory 320 may be at least in part accessible to processor 310. Memory 320 may be at least in part comprised in processor 310. Memory 320 may be means for storing information. Memory 320 may comprise computer instructions that processor 310 is configured to execute. When computer instructions configured to cause processor 310 to perform certain actions are stored in memory 320, and device 300 overall is configured to run under the direction of processor 310 using computer instructions from memory 320, processor 310 and/or its at least one processing core may be considered to be configured to perform said certain actions. Memory 320 may be at least in part comprised in processor 310. Memory 320 may be at least in part external to device 300 but accessible to device 300.

Device 300 may comprise a transmitter 330. Device 300 may comprise a receiver 340. Transmitter 330 and receiver 340 may be configured to transmit and receive, respectively, information in accordance with at least one cellular or non-cellular standard. Transmitter 330 may comprise more than one transmitter. Receiver 340 may comprise more than one receiver. Transmitter 330 and/or receiver 340 may be configured to operate in accordance with global system for mobile communication, GSM, wideband code division multiple access, WCDMA, long term evolution, LTE, IS-95, wireless local area network, WLAN, Ethernet and/or worldwide interoperability for microwave access, WiMAX, standards, for example.

Device 300 may comprise a near-field communication, NFC, transceiver 350. NFC transceiver 350 may support at least one NFC technology, such as NFC, Bluetooth, Wibree or similar technologies.

Device 300 may comprise user interface, UI, 360. UI 360 may comprise at least one of a display, a keyboard, a touchscreen, a vibrator arranged to signal to a user by causing device 300 to vibrate, a speaker and a microphone. A user may be able to operate device 300 via UI 360, for example to request for a route-based activity session and/or to place voice calls, where applicable, for example.

Device 300 may comprise or be arranged to accept a user identity module 370. User identity module 370 may comprise, for example, a subscriber identity module, SIM, card installable in device 300. A user identity module 370 may comprise information identifying a subscription of a user of device 300. A user identity module 370 may comprise cryptographic information usable to verify the identity of a user of device 300 and/or to facilitate encryption of communicated information and billing of the user of device 300 for communication effected via device 300.

Processor 310 may be furnished with a transmitter arranged to output information from processor 310, via electrical leads internal to device 300, to other devices comprised in device 300. Such a transmitter may comprise a serial bus transmitter arranged to, for example, output information via at least one electrical lead to memory 320 for storage therein. Alternatively to a serial bus, the transmitter may comprise a parallel bus transmitter. Likewise processor 310 may comprise a receiver arranged to receive information in processor 310, via electrical leads internal to device 300, from other devices comprised in device 300. Such a receiver may comprise a serial bus receiver arranged to, for example, receive information via at least one electrical lead from receiver 340 for processing in processor 310. Alternatively to a serial bus, the receiver may comprise a parallel bus receiver.

Device 300 may comprise further devices not illustrated in FIG. 3. For example, where device 300 comprises a smartphone, it may comprise at least one digital camera. Some devices 300 may comprise a back-facing camera and a front-facing camera, wherein the back-facing camera may be intended for digital photography and the front-facing camera for video telephony. Device 300 may comprise a fingerprint sensor arranged to authenticate, at least in part, a user of device 300. In some embodiments, device 300 lacks at least one device described above. For example, some devices 300 may lack a NFC transceiver 350 and/or user identity module 370.

Processor 310, memory 320, transmitter 330, receiver 340, NFC transceiver 350, UI 360 and/or user identity module 370 may be interconnected by electrical leads internal to device 300 in a multitude of different ways. For example, each of the aforementioned devices may be separately connected to a master bus internal to device 300, to allow for the devices to exchange information. However, as the skilled person will appreciate, this is only one example and depending on the embodiment various ways of interconnecting at least two of the aforementioned devices may be selected without departing from the scope of the present invention.

Figure 4:
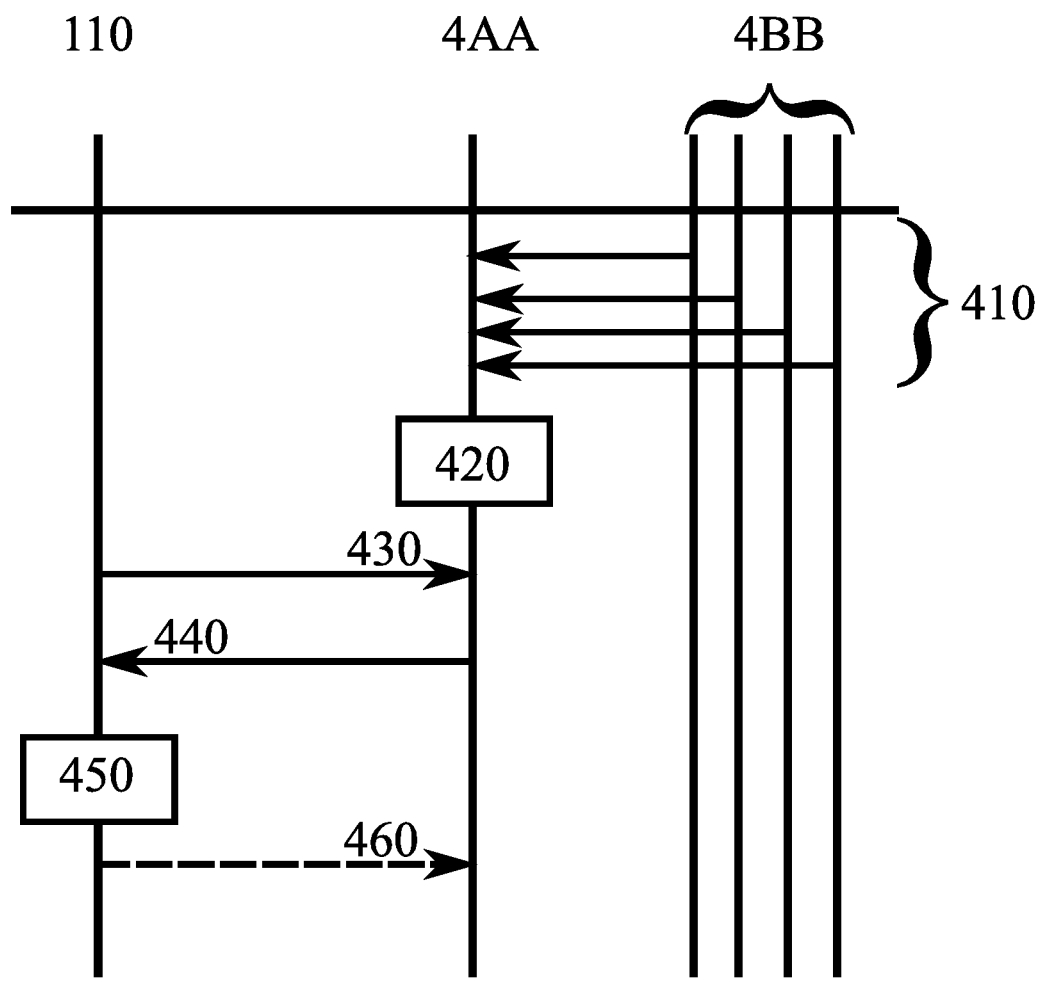
FIG. 4 illustrates signalling in accordance with at least some embodiments of the invention.

FIG. 4 illustrates signalling in accordance with at least some embodiments of the invention. On the vertical axes are disposed, from left to right, device 110 of FIGS. 1A and 1B, server 4AA and further users 4BB. In general further users 4BB comprise a set of users other than the user of device 110, although the user of device 110 may in some cases be comprised in the set of further users 4BB.

In collective phase 410, which may take place over a period of time, the period of time preceding the other phases of the figure possibly by a several months or more, further users 4BB provide to server 4AA indications of their locations and activity types that are selected, implicitly or explicitly, in those locations. For example, these indications may relate to activity types of activity sessions the further users are engaged in, as well as corresponding locations, enabling server 4AA to associate the activity types with the corresponding sessions by constructing a thematic map database.

In phase 420, server 4AA may construct or update a thematic map database based on the indications received in phase 410, and/or indications otherwise obtained in server 4AA. The thematic map database may comprise a heat map, for example. The thematic map database associates activity types with locations, enabling determination of statistical intensities for activity types as a function of location. In some embodiments, the thematic map database also comprises at least some route information, such as a set of outdoor activity routes that are available in a certain city.

In phase 430, device 110 queries the database by transmitting a query to the server, the query comprising an implicit or explicit indication of a location of device 110. Responsively, in phase 440, server 4AA transmits back to device 110 a set of activity types that are associated with the location, area and/or surroundings of device 110.

Phase 450 comprises determining a route, based at least partially on the set of activity types received in phase 440, and presenting the route to the user as a suggested route. Determining the route has been described above.

Optional phase 460 comprises transmitting to server 4AA an indication of an activity type the user selects, which may be, but need not be, the suggested activity type. The message of phase 460 may also comprise an indication of the current location of device 110.

Alternatively to the phases described above, device 110 may request in phase 430 for server 4AA to determine the route, such that device 110 in phase 430 provides its current location and the activity type the route is to involve. Server 4AA may then responsively determine the route based at least partly on the thematic map and the information in the request of phase 430. In these embodiments, the route is informed to device 110 in phase 440.

As a yet further alternative, device 110 may in phase 430 query for areas that are associated in the thematic map database with an activity type, the query of phase 430 comprising an indication of the activity type. The areas, once informed to device 110 in phase 440, then enable device 110 to determine the route in a way that the route traverses an area that is associated with the correct activity type.

Figure 5:
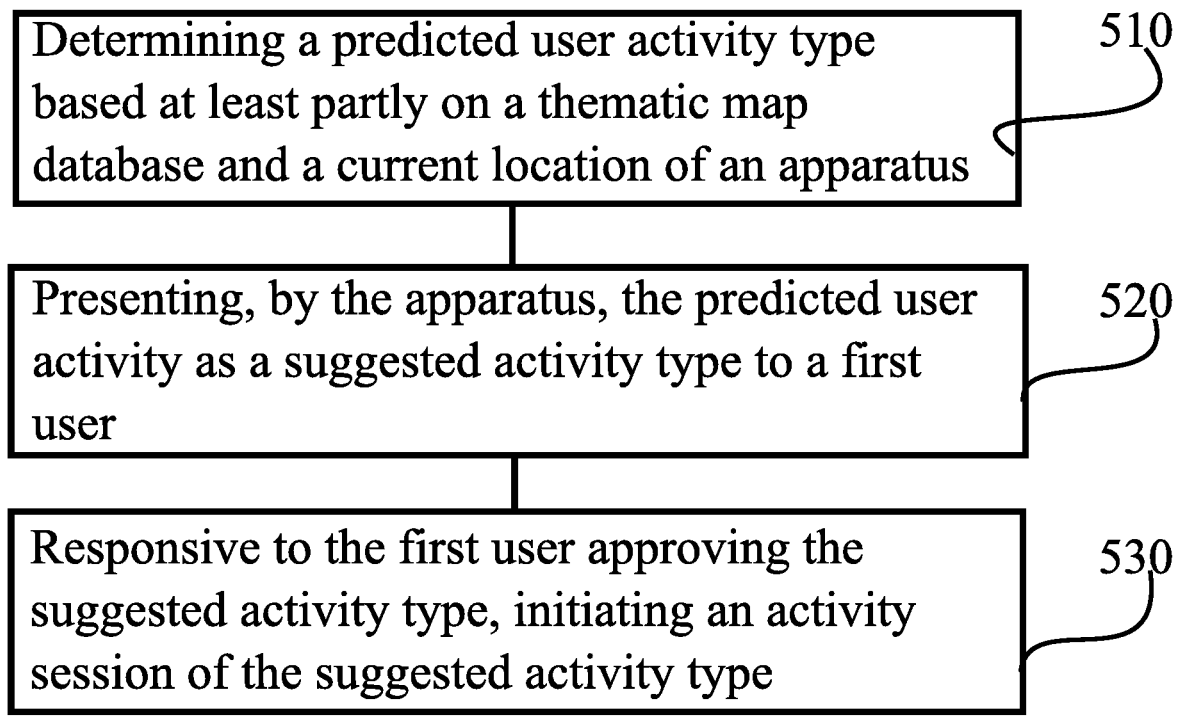
FIG. 5 is a flow graph of a method in accordance with at least some embodiments of the present invention.

FIG. 5 is a flow graph of a method in accordance with at least some embodiments of the present invention. The phases of the illustrated method may be performed in device 110, for example, or in a control device configured to control the functioning of device 110, when implanted therein, for example.

Phase 510 comprises determining a predicted user activity type based at least partly on a thematic map database and a current location of an apparatus. Phase 520 comprises presenting, by the apparatus, the predicted user activity type as a suggested activity type to a first user. Finally, phase 530 comprises, responsive to the first user approving the suggested activity type, initiating an activity session of the suggested activity type It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in enhancing device usability and/or personal safety.

REFERENCE SIGNS LIST

| | |
|---|---|
| 110 | Device |
| 110x | Auxiliary device |
| 120 | Base station |
| 130 | Network node |
| 140 | Network |
| 150 | Satellite constellation |
| 200 | Display |
| 210 | System level display |
| 220 | Map |
| 230 | Start point |
| 240 | Route |
| 310-370 | Elements of FIG. 3 |
| 410-460 | Phases of the signalling illustrated in FIG. 4 |
| 510-530 | Phases of the method of FIG. 5 |

The invention claimed is:

1. An apparatus comprising at least one processing core, at least one memory including computer program code, the at least one memory and the computer program code being configured to, with the at least one processing core, cause the apparatus at least to:
   determine a predicted route for an exercise session;
   repeatedly update the predicted route based on movement of the apparatus, such that the updated route comprises an already traversed section and a predicted section;
   responsive to the already traversed section arriving at a first intersection, present to the user first labelled options concerning sub-routes from the first intersection, determine based on movement of the apparatus which of the first labelled options the user chooses, and
   responsive to the already traversed section arriving at a second intersection, present to the user second labelled options concerning sub-routes from the second intersection.

2. The apparatus according to claim 1, wherein the apparatus is configured to determine the predicted route based at least partly on an exercise history of a user and a current location of the apparatus.

3. The apparatus according to claim 1, wherein the labels indicate at least one of: a total route length obtainable via the respective sub-route, a total exercise session duration obtainable via the respective sub-route, a speed obtainable via the respective sub-route and a metabolic effect obtainable via the respective sub-route.

4. The apparatus according claim 1, wherein the apparatus is configured to compile the first labelled options and/or the second labelled options based on the exercise history of a user.

5. The apparatus according to claim 4, wherein the apparatus is configured to compile the first labelled options and the second labelled options such that one of the options at each intersection corresponds to the predicted route, and other options at each intersection represent deviations from the predicted route in terms of length, duration, speed or metabolic effect.

6. The apparatus according to claim 1, wherein the at least one memory and the computer program code are configured to, with the at least one processing core, cause the apparatus to determine the predicted route based at least partly on at least one of the following: a thematic map database, a season of the year, a time of day, user settings of the user, history information of the user, elevation information and a location of the apparatus.

7. The apparatus according to claim 6, wherein user settings of the user comprise settings relating to at least one of the following:
   a desired energy consumption of a physical exercise session;
   a desired cardiovascular effect of the physical exercise session;
   a desired oxygen consumption effect of the physical exercise session;
   a desired EPOC effect of the physical exercise session;
   a desired recovery time length of the physical exercise session, and
   an indication the user wishes the route to be conveniently interruptible.

8. The apparatus according to claim 7, wherein the energy consumption comprises an increased energy consumption in the user's body, the increase being due to the physical exercise comprised in the physical exercise session.

9. A method in an apparatus, comprising:
   determining a predicted route for an exercise session;
   repeatedly updating the predicted route based on movement of the apparatus, such that the updated route comprises an already traversed section and a predicted section;
   responsive to the already traversed section arriving at a first intersection, presenting to the user first labelled options concerning sub-routes from the first intersection, determining based on movement of the apparatus which of the first labelled options the user chooses, and
   responsive to the already traversed section arriving at a second intersection, presenting to the user second labelled options concerning sub-routes from the second intersection.

10. The method according to claim 9, wherein the predicted route is determined based at least partly on an exercise history of a user and a current location of the apparatus.

11. The method according to claim 9, wherein the labels indicate at least one of: a total route length obtainable via the respective sub-route, a total exercise session duration obtainable via the respective sub-route, a speed obtainable via the respective sub-route and a metabolic effect obtainable via the respective sub-route.

12. The method according to claims 9, further comprising compiling the first labelled options and/or the second labelled options based on the exercise history of a user.

13. The method according to claim 12, further comprising compiling the first labelled options and the second labelled options such that one of the options at each intersection corresponds to the predicted route, and other options at each intersection represent deviations from the predicted route in terms of length, duration, speed or metabolic effect.

14. The method according to claim 9, further comprising determining the predicted route based at least partly on at least one of the following: a thematic map database, a season of the year, a time of day, user settings of the user, history information of the user, elevation information and a location of the apparatus.

15. The method according to claim 13, wherein user settings of the user comprise settings relating to at least one of the following:
   a desired energy consumption of a physical exercise session;
   a desired cardiovascular effect of the physical exercise session;
   a desired oxygen consumption effect of the physical exercise session;
   a desired EPOC effect of the physical exercise session;
   a desired recovery time length of the physical exercise session, and
   an indication the user wishes the route to be conveniently interruptible.

16. The method according to claim 15, wherein the energy consumption comprises an increased energy consumption in the user's body, the increase being due to the physical exercise comprised in the physical exercise session.

17. A non-transitory computer readable medium having stored thereon a set of computer readable instructions that, when executed by at least one processor, cause an apparatus to at least:
   determine a predicted route for an exercise session;
   repeatedly update the predicted route based on movement of the apparatus, such that the updated route comprises an already traversed section and a predicted section;
   responsive to the already traversed section arriving at a first intersection, present to the user first labelled options concerning sub-routes from the first intersection, determine based on movement of the apparatus which of the first labelled options the user chooses, and
   responsive to the already traversed section arriving at a second intersection, present to the user second labelled options concerning sub-routes from the second intersection.

\* \* \* \* \*